United States Patent
Nagai et al.

(10) Patent No.: US 9,903,852 B2
(45) Date of Patent: Feb. 27, 2018

(54) METHOD FOR NON-DESTRUCTIVE JUDGMENT OF PEARL QUALITY

(76) Inventors: Kiyohito Nagai, Shima (JP); Junichi Hiramatsu, Ise (JP); Yasunori Iwahashi, Toba (JP)

(*) Notice: Subject to any disclaimer, the term of this patent is extended or adjusted under 35 U.S.C. 154(b) by 389 days.

(21) Appl. No.: 12/983,993

(22) Filed: Jan. 4, 2011

(65) Prior Publication Data

US 2012/0050526 A1 Mar. 1, 2012

(30) Foreign Application Priority Data

Aug. 24, 2010 (JP) ................. 2010-187465

(51) Int. Cl.
| | |
|---|---|
| H04N 7/18 | (2006.01) |
| G01N 33/38 | (2006.01) |
| G01N 21/55 | (2014.01) |
| G01N 21/64 | (2006.01) |
| G01N 21/87 | (2006.01) |
| G01N 21/95 | (2006.01) |

(52) U.S. Cl.
CPC .......... *G01N 33/381* (2013.01); *G01N 21/55* (2013.01); *G01N 21/6456* (2013.01); *G01N 21/87* (2013.01); *G01N 21/95* (2013.01); *G01N 2021/6417* (2013.01)

(58) Field of Classification Search
CPC .... G01N 21/55; G01N 21/6456; G01N 21/95; G01N 33/381; G01N 21/87; G01N 2021/6417; A61B 5/417; H01J 37/252
USPC ..................... 348/125, 130; 435/68; 424/9.1; 600/476; 250/310, 504 R; 702/19
See application file for complete search history.

(56) References Cited

U.S. PATENT DOCUMENTS

| | | | | |
|---|---|---|---|---|
| 6,124,600 | A * | 9/2000 | Moroishi et al. | 250/504 R |
| 6,201,241 | B1 * | 3/2001 | Koike | H01J 37/252 |
| | | | | 250/310 |
| 2007/0020181 | A1* | 1/2007 | Workman et al. | 424/9.1 |
| 2008/0132793 | A1* | 6/2008 | Kollias et al. | 600/476 |
| 2010/0034743 | A1* | 2/2010 | Cohen et al. | 424/9.1 |
| 2010/0075374 | A1* | 3/2010 | Lim et al. | 435/68.1 |
| 2010/0280762 | A1* | 11/2010 | Maier | A61B 5/417 |
| | | | | 702/19 |

FOREIGN PATENT DOCUMENTS

| | | | |
|---|---|---|---|
| JP | 2005102629 A | | 4/2005 |
| JP | 2006118923 A | * | 5/2006 |

(Continued)

OTHER PUBLICATIONS

Machine translation of JP 2006118923 A.*

(Continued)

*Primary Examiner* — Mohammed Rahaman
*Assistant Examiner* — Richard Carter

(57) ABSTRACT

The present invention relates to a method for non-destructive judgment of pearl quality by measuring the ultraviolet-visible reflectance spectrum and/or ultraviolet-visible fluorescence spectrum of a pearl or pearl shell to be inspected and comparing the values obtained with those preliminarily measured for a normal pearl or pearl shell. The present invention also relates to a non-destructive inspection apparatus of pearl quality. According to the present invention, the quality of the aimed pearl or pearl shell can be easily and rapidly judged under a non-destructive condition.

7 Claims, 8 Drawing Sheets

(56) References Cited

FOREIGN PATENT DOCUMENTS

| JP | 2008261885 A | 10/2008 |
|---|---|---|
| WO | 99061890 A1 | 12/1999 |

OTHER PUBLICATIONS

Yasunori Matsuda and Tadaki Miyoshi, "Effects of gamma-Ray Irradiation on Colour and Fluorescence of Pearls", 1988, Japanese Journal of Applied Physics, 27 (2), pp. 235-239.*
Noldy Gustaf F. Mamangkey, Snezana Agatonovic, and Paul C. Southgage, "Assessing Pearl Quality Using Reflectance UV-VIS Spectroscopy: Does The Same Donor Produce Consistent Pearl Quality?", (Marine Drugs. 2010; 8(9): 2517-2525, published online Sep. 20, 2010. doi 10.3390/md8092517, https://www.ncbi.nlm.nih.gov/pmc/articles/PMC2953399/.*
Shane Elen, Spectral Reflectance and Fluorescence Characteristics of Natural-Color and Heat-Treated "Golden" South Sea Cultured Pearls, Summer 2001, Gems & Gemology, vol. 37, No. 2, pp. 114-123, https://www.gia.edu/gems-gemology/summer-2001-heat-treated-golden-south-sea-cultured-pearls-elen.*
Yasunori Matsuda and Tadaki Miyoshi, "Effects of gamma-Ray Irradiation on Colour and Fluorescence of Pearls", 1988, Japanese Journal of Applied Physics, 27(2), pp. 235-239.*
Mamangkey Noldy "Improving the Quality of Pearls From Pinctada Maxima" 2009 James Cook University, AU, pp. 139-152.
Miyoshi, T., "Effects of Light Irradiation on Fluorescence and Optical Reflectance of Pearls" 1992 Technol Rep Yamaguchi Univ, vol. 5, No. 1, pp. 23-30.
Matsuda, et al., "Effects of Gamma-Ray Irradiation on Colour and Fluorescence of Pearls" 1988 JP Journal of Applied Physics, vol. 27, No. 2, pp. 1-10.
Hiramatsu, et al., "Non-Destructive Assessment of the Effects of Heat and Sunlight on Akoya Pearl Quality" 2010 Seibutsu-Kogaku, vol. 88, No. 8, pp. 378-383.
Extended European Search Report dated Dec. 23, 2011 for Application No. 11150124.3.
China Patent Office, First Notice of Opinion on Examination, Application No. 201080002848.8, dated Dec. 27, 2013, 14 pages.
Japan Patent Office, Notification of Reason for Rejection, Application No. 2010-187465, dated Mar. 14, 2014, 7 pages.
Japan Patent Office, Notification of Reason for Rejection, Application No. 2010-187465, dated Jul. 29, 2014, 6 pages.
China Patent Office, Office Action, Application No. 201080002848.8, dated Oct. 27, 2015.
Hiuichun, Song et al., "Fluorescence spectrum analysis of fresh water pipless pearl," 1998, Journal of Fishery Sciences of China, vol. 5, No. 4.

\* cited by examiner

METHOD FOR NON-DESTRUCTIVE JUDGMENT OF PEARL QUALITY

REFERENCE TO THE RELATED APPLICATION

The present application is based on the previous Japanese Patent Application No. 2010-187465 filed on Aug. 24, 2010 and claims the profits of its priority, and all of the entities of its disclosure are incorporated herein by reference.

BACKGROUND OF THE INVENTION

Field of the Invention

The present invention relates to a method for non-destructive judgment of pearl quality.

Related Art

Pearls such as Akoya pearl (pearl from *Pinctada fucata*), Silver lipped pearl (pearl from Pinctada maxima), Black lipped pearl (pearl from *Pinctada margaritifera*), Mabe pearl (pearl from *Pteria penguin*), and Fresh water pearl are constituted from a nacre structure consisting of the calcium carbonate crystal of aragonite having a size of about 200 to 700 nm and the multilayered film of scleroproteins (matrix proteins), and pearl luster peculiar to pearls are produced by this multilayered film structure.

Among organic matrices in pearls having a generic name of conchiolin, the nacreous shell matrix proteins (NSMPs) play an important role of adhering calcium carbonate crystals for retaining the nacre structure. If this protein is destructed (or damaged) by some causes such as light, heat or chemicals, the crystals of calcium carbonate are gradually broken and the crystal layer are peeled off, thus resulting in the disappearance of pearl luster. Such influences are actualized together with the passage of time. The effects on the aging deterioration of pearls depend on the degrees of damage to the protein in pearl, and thus the severer the damage to the matrix protein in the nacre is, the more liable to be caused the aging deteriorations such as the decline of pearl luster is.

The pearls immediately after destruction of their proteins maintain pearl luster until the peeling of the nacre begins, but the peeling of the nacre is actualized with the passage of time. It is thus predicated almost impossible to judge visually the deterioration of the pearl protein due to some causes as far as the peeling of the nacre is not actualized.

Also, some of cultured pearls commercially available as finished goods may be the ones which have been subjected to a processing defined as "bringing out the potential beauty of natural or cultured pearls by physical or chemical methods, or changing their colors or appearances irrespective of their inherent properties" according to "Pearl Standard" (2009) by Japan Pearl Promotion Society, Inc. Some of these processed pearls have been notably deteriorated in the pearl protein due to processing, and some will lose pearl luster within a comparatively short period of time. Excessively processed pearls are strikingly damaged to the nacre to give peeling spots around the surface of the nacre. It is possible to distinguish these peeling spots by the visual inspection by professional skilled testers. However, it is extremely difficult even for skilled testers to distinguish the peeling spots by visual judgment as for the test of pearls immediately after processing of which the peeling of the nacre is not yet actualized.

Aging deterioration occurs at an early stage in pearls damaged to the protein of the nacre by the excessive processing, and thus the durability of pearls as jewels may be impaired.

On the other hand, the evaluation of properties of pearl protein is demanded to be conducted non-destructively so that the value of the pearl as a jewel will not be impaired.

There have been described several methods for non-destructively inspecting the quality of pearls.

For example, Japanese Patent Laid-Open Publication No. H10(1998)-260136 discloses a method for testing minute defects as the internal structural information of pearls by irradiating with light at a certain wavelength such as 488 nm and the like. This method aims at the detection and evaluation of physical damages and defects such as the internal defects of pearls, and no examination is aimed at as regards the state of nacreous matrix proteins such as conchiolin.

Also, Japanese Patent Laid-Open Publication No. 2006-118923 discloses the non-destructive judgment of the grade of pearl oysters. In this method, the orientation of aragonite crystals in the nacre of a pearl is measured by the X-ray diffraction method for evaluating the quality of the pearl. However, in this method, the state of nacreous matrix proteins such as conchiolin is not examined, and besides the measurement is conducted by using the X-ray diffraction method.

Therefore, there have been still demanded a method for judging non-destructively and obtaining the result by easily and rapidly measuring the quality of pearls.

SUMMARY OF THE INVENTION

The present inventors have now paid their attention to the properties of the nacre at the time of evaluating the quality of pearls or pearl shells. The present inventors have successfully measured and digitized the deterioration of nacreous proteins without destroying or impairing pearls or pearl shells by using the ultraviolet-visible reflection spectrum and ultraviolet-visible fluorescence spectrum of the pearls or pearl shells. Further, the present inventors have succeeded in rapidly and easily evaluating the degree of the deterioration of the pearls or pearl shells and judging the processing types. The present invention is thus based on these findings.

Thus, the object of the present invention is to provide a process and an inspection apparatus for easily and rapidly judging the quality of an aimed pearl or pearl shell under a nondestructive condition.

According to the present invention, there are provided the following judgment methods and inspection apparatuses:
(1) a method for non-destructive judgment of pearl quality, by measuring the ultraviolet-visible reflection spectrum and/or ultraviolet-visible fluorescence spectrum of a pearl or pearl shell to be inspected and comparing the values with those preliminarily measured for a normal pearl or pearl shell;
(2) a method according to (1) described above, wherein the reflection spectrum and/or fluorescence spectrum of nacreous proteins of the pearl or pearl shell to be inspected are measured;
(3) a method according to (1) or (2), wherein the degree of the deterioration of the pearl or pearl shell to be inspected is judged;
(4) a method according to any one of (1) to (3) described above, which comprises judging whether the deterioration of the pearl or pearl shell to be inspected is due to heat treatment or sunlight irradiation, by evaluating the combination of the measurement obtained from the ultraviolet-visible reflection spectrum of the pearl or pearl shell to be inspected and the measurement obtained from the ultraviolet-visible fluorescence spectrum of the pearl or pearl shell to be inspected;

(5) a method according to any one of (1) to (4) described above, wherein the spectral reflectance of the pearl or pearl shell in the range of 230 to 475 nm is measured as the reflection spectrum;

(6) a method according to any one of (1) to (5) described above, wherein the spectral reflectance in the range of 250 to 260 nm (Ra) and the spectral reflectance in the range of 270 to 290 nm (Rb) were measured as the reflection spectrum to obtain the ratio (spectral reflectance ratio R (a/b)) or difference thereof for judgment based on this result;

(7) a method according to any one of (1) to (6) described above, wherein a fluorescence intensity of the fluorescence spectrum in the range of 320 to 360 nm generated by irradiating the pearl or pearl shell with ultraviolet light in the range of 250 to 300 nm as the excitation light is measured;

(8) a method according to any one of (1) to (7) described above, wherein a fluorescence intensity of the fluorescence spectrum in the range of 400 to 550 nm generated by irradiating the pearl or pearl shell with ultraviolet light in the range of 250 to 400 nm as the excitation light is measured;

(9) a method according to (7) or (8) described above, wherein fluorescence generated by ultraviolet irradiation is photographed by a CCD camera equipped with an optical filter through which light in the range of 320 to 360 nm, 420 to 460 nm or 400 to 550 nm is transmitted, and the result is digitized for judgment based on this result;

(10) a non-destructive inspection apparatus of pearl quality, comprising a light irradiation part for irradiating a pearl or pearl shell with light from an ultraviolet light source, and a fluorescence detector for measuring the fluorescence generated by ultraviolet irradiation from the light irradiation part;

(11) an apparatus according to (10) described above, which further comprises a spectral reflectance detector for measuring the spectral reflectance of the pearl or pearl shell to the ultraviolet irradiation from the light irradiation part;

(12) an apparatus according to (10) or (11), which further comprises an analyzer for judging the degree of the deterioration of the pearl or pearl shell to be inspected by comparing the data obtained in the detection part described above with the data of a normal pearl or pearl shell preliminarily measured;

(13) an apparatus according to (12), which further comprises an arrangement part for arranging the pearl or pearl shell to be inspected, and a display for displaying the outputs of the analyzer described above;

(14) an apparatus according to any one of (10) to (13) described above, wherein fluorescence detector is provided with a CCD camera equipped with an optical filter through which light in the range of 320 to 360 nm, 420 to 460 nm or 400 to 550 nm is transmitted, wherein the CCD camera is one for photographing the fluorescence generated by ultraviolet irradiation;

(15) an apparatus according to any one of (10) to (14) described above, wherein the light irradiated from the light irradiation part has a wavelength of 230 to 475 nm; and

(16) an apparatus according to any one of (10) to (15) described above, wherein the outputs from the analyzer are displayed on the display by color classification according to the degrees of the deterioration of the pearls or pearl shells.

According to the judgment method or inspection apparatus of the present invention, the quality of pearls can be rapidly and easily measured under a non-destructive condition without destruction of the pearl or pearl shell. The apparatus of the present invention may be miniaturized and easily operated, so that it can be used in a spot of selling pearls and the like. Thus, it has hitherto been unknown as far as the present inventors know to be capable of measuring rapidly and easily the quality of pearls, and thus it can be said that the judgment method and inspection apparatus are epoch-making.

BRIEF DESCRIPTION OF THE DRAWINGS

In FIG. 1, "A" represents the results in the heat treatment zone, and "B" represents the results of the sunlight irradiation zone. Also in FIG. 1, the bold line indicate the results before treatment, the dotted line indicate the result after 6 hours, the broken line indicate the result after 192 hours, and the fine solid line indicate the results after 768 hours.

In FIG. 3, "A" represents the results in the heat treatment zone, and "B" represents the results of the sunlight irradiation zone. Also in FIG. 1, the bold line indicate the results before treatment, the dotted line indicate the results after 6 hours, the broken line indicates the results after 192 hours, and the fine solid line indicate the results after 768 hours.

DETAILED DESCRIPTION OF THE INVENTION

Figure 1A:
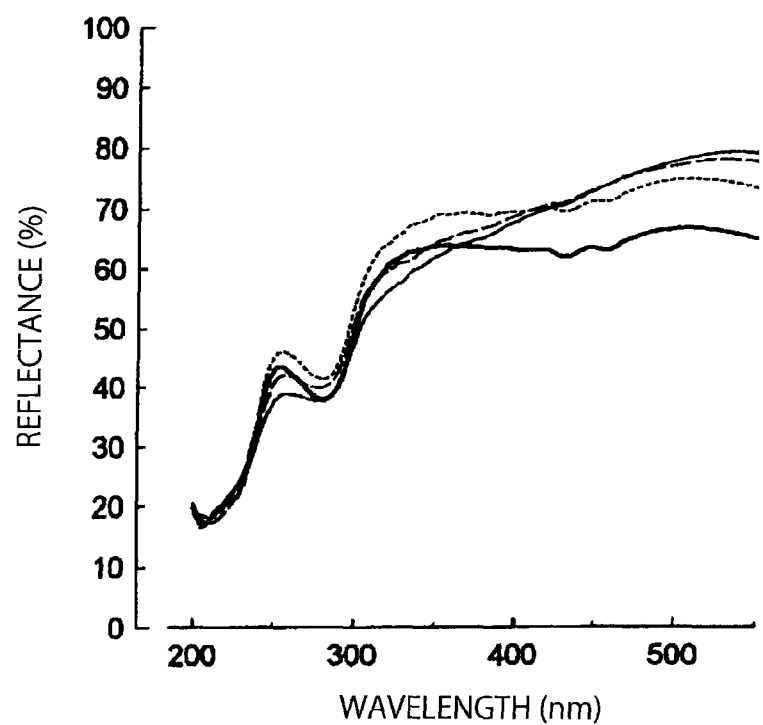
FIG. 1 shows the measurements of the reflectance spectrum in Example 1.

The present invention, as described above, relates to a method for non-destructive judgment of pearl quality, by measuring the ultraviolet-visible reflection spectrum and/or ultraviolet-visible fluorescence spectrum of a pearl or pearl shell to be inspected and comparing the values with those preliminarily measured for a normal pearl or pearl shell.

That is, the judgment method according to the present invention is capable of judging the quality of pearls under a non-destructive condition without impairing the pearls or pearl shells or scraping a part of a sample.

The pearl herein is not specifically limited and generally include pearls such as cultured pearl, natural pearl, Keshi, blister and blister pearl, typically Akoya pearl, Silver lipped pearl, Black lipped pearl, Mabe pearl and Fresh water pearl.

Also, the pearl shell herein means the shell of pearl oyster, particularly the nacre part of the shell.

In this connection, the quality of pearls means the quality of pearls in the case of evaluating the pearl or pearl shell from the ornamental standpoint, and such quality of the pearls is specifically affected by the states of nacreous proteins of the pearl or pearl shell and herein means the quality relating to nacreous proteins. The quality of pearls in this meaning includes, for example, the one which is considered from the standpoint of the color, luster, depth of color, scratches, and the like of the pearl or pearl shell.

Also, when the quality has been deteriorated, the degree of deterioration is also included in the quality to be judged. Further, the cause of the quality deterioration may also be judged. In this case, the cause of the quality deterioration of pearls may include quality deterioration by processing, quality deterioration by aging and the like. The main causes of the former quality deterioration by processing may include, for example, heat treatment in processing, bleaching treatment with oxidizing agents or reducing agents, coloring treatment with chemical agents such as silver nitrate, colorants and dyes, treatment with a fluorescent brightener, treatments with chemical agents such as alkali solvents and organic solvents, and the like. Also, the main causes of the latter quality deterioration by aging may include the deterioration by sunlight irradiation, which may be considered to proceed with the passage of time.

Thus, as a preferred embodiment of the present invention, the degree of the deterioration in a pearl or pearl shell to be inspected is judged in the judgment method of the present invention.

According to one preferred embodiment of the present invention, the spectral reflectance spectrum and/or fluorescence spectrum of the nacreous proteins of the pearl or pearl shell to be inspected is measured in the judgment method of the present invention.

In the present invention, the ultraviolet-visible reflection spectrum and/or ultraviolet-visible fluorescence spectrum of the pearl or pearl shell to be inspected according to the judgment method are measured, and the values (results) obtained are compared with the values (results) of the normal pearl or pearl shell which have preliminarily been measured.

In this connection, the spectral value (result) of the normal pearl or pearl shell which has preliminarily been measured mean the value (referred to hereinafter as the "normal value" or "control value") that a pearl or pearl shell which is known to be normal, particularly normal as regards nacreous proteins is prepared to measure and maintain the ultraviolet-visible spectral reflectance spectrum and/or ultraviolet-visible fluorescence spectrum of the pearl or pearl shell prior to the practice of the judgment method. This value is used in the practice of the judgment method of the present invention. If the influence of the kinds or the measurement conditions of the pearl or pearl shell may be apprehended, it is desirable to find a normal value preliminarily under the same kind and measurement condition of the pearl or pearl shell as the actual judgment condition.

Also, in the judgment method of the present invention, the phraseology "the ultraviolet-visible reflection spectrum and/or ultraviolet-visible fluorescence spectrum of the pearl or pearl shell to be inspected according to the judgment method are measured" includes both of the measurements of either one of "the ultraviolet-visible reflection spectrum" or "ultraviolet-visible fluorescence spectrum" of the pearl or pearl shell to be inspected and of the measurement of the combination of these spectra. Also, the term "from ultraviolet zone to visible zone" (ultraviolet-visible zone) is used in a meaning of all spectral ranges including in addition to the range from ultraviolet zone to visible zone, the range in only the ultraviolet zone and the range in only visible zone.

According to one preferred embodiment of the present invention, the spectral reflectance of the pearl or pearl shell in the range of 230 to 475 nm is measured as the spectral reflectance spectrum in the judgment method of the present invention. The wavelength described above is preferably in the range of 230 to 400 nm, more preferably 230 to 320 nm, further preferably 240 to 300 nm, further more preferably 250 to 290 nm, and particularly 250 to 286 nm.

In this connection, the spectral reflection (reflectance) spectrum of the pearl or pearl shell may be measured with usual apparatuses such as a spectrophotometer or a multi-photometric apparatus.

According to one more preferred embodiment of the present invention, in the judgment method of the present invention, a spectral reflectance (Ra) in the range of 250 to 260 nm and a spectral reflectance (Rb) in the range of 270 to 290 nm are measured as the spectral reflectance spectrum to obtain the ratio (spectral reflectance ratio R (a/b)) or the difference thereof and thus the judgment is conducted on the basis of the ratio or difference. Particularly preferably, the spectral reflectance (Ra) at a wavelength of about 254 nm and the spectral reflectance (Rb) at a wavelength of about 282 nm are measured to obtain the ratio (spectral reflectance ratio $R_{254/282}$) or the difference thereof and thus the judgment is conducted on the basis of the ratio or difference.

According to another preferred embodiment of the present invention, in the judgment method of the present invention, the fluorescence intensity in the range of 320 to 360 nm (preferably 330 to 350 nm) generated by irradiating a pearl or pearl shell with the ultraviolet light in the range of 250 to 300 nm (preferably 270 to 290 nm) as an excitation light is measured as fluorescence spectrum. According to a particularly preferred embodiment of the present invention, the fluorescence intensity at a wavelength of 340 nm ($FI_{340}$) generated by irradiating the pearl or pearl shell with the ultraviolet light at a wavelength of around 280 nm as an excitation light is measured as the measurement of the fluorescence spectrum in the ultraviolet zone of a pearl or pearl shell.

According to another preferred embodiment of the present invention, in the judgment method of the present invention, the fluorescence intensity in the range of 400 to 550 nm (preferably 400 to 500 nm, more preferably 410 to 480 nm) generated by irradiating a pearl or pearl shell with the ultraviolet light in the range of 250 to 400 nm (preferably 320 to 380 nm) as an excitation light is measured as the measurement of fluorescence spectrum. According to a particularly preferred embodiment of the present invention, the fluorescence intensity in the range of about 420 to 460 nm generated by irradiating a pearl or pearl shell with the ultraviolet light in the range of around 365 nm as an excitation light is measured as the measurement of the fluorescence spectrum in the visible zone of a pearl or pearl shell.

In this connection, fluorescence in the ultraviolet zone and fluorescence in the visible zone may be measured with a usual spectrofluorophotometer.

According to another preferred embodiment of the present invention, the judgment method of the present invention includes the judgment whether the deterioration of the quality of a pearl or pearl shell to be inspected is due to heat treatment or sunlight irradiation by evaluating the measurements of the ultraviolet-visible spectral reflectance spectrum in combination with the measurements of the ultraviolet-visible fluorescence spectrum of the sample.

In the present invention, when the fluorescence spectrum of a pearl or pearl shell is measured to judge the quality, it is possible to use whole spectrum but it is desirable to measure the fluorescence intensity at a certain wavelength described above. In order to measure the fluorescence spectrum in such a certain wavelength, it will be capable of efficient measurement by using an optical filter, preferably a band-path filter in which a wavelength band is set up. In order to digitize or image the results obtained, it is effective to photograph the fluorescence with a CCD camera equipped with an optical filter (for example, band-path filter) and, if necessary, to subject it to image processing for use.

Thus, according to another more preferred embodiment of the present invention, the fluorescence generated by ultraviolet irradiation in the judgment method of the present invention is photographed with a CCD camera equipped with an optical filter (for example, band-path filter) which transmits the wavelengths in the range of 320 to 360 nm, 420 to 460 nm or 400 to 550 nm, and the results are digitized and judged on the basis of the digitized results. Rapid inspection of a large amount of pearls or pearl shells can be realized in this manner.

According to another embodiment of the present invention, there is provided, as described above, a non-destructively inspection apparatus comprising a light irradiation part for irradiating a pearl or pearl shell with the light from an ultraviolet light source, and a fluorescence detector for measuring fluorescence generated by ultraviolet irradiation from the light irradiation part described above.

According to another preferred embodiment of the present invention, the apparatus according to the present invention further comprises an analyzer for judging the deterioration degree of a pearl or pearl shell to be inspected by comparing the data obtained in the detection part described above with the data of a normal pearl or pearl shell preliminarily measured.

According to another more preferred embodiment of the present invention, the apparatus according to the present Invention further comprises an arrangement part for arranging the pearl or pearl shell to be inspected, and a display for displaying the outputs of the analyzer described above.

In this connection, the arrangement part can arrange the pearl or pearl shell to be inspected, and the number and kind of the pearl or pearl shell which can be arranged is not specifically limited. Also, the method of arrangement is not limited specifically, and the arrangement part may be, for example, a flat sample table on which a sample can be arranged at regular intervals in a planar form or a plain on which a pearl necklace or work or a pearl or pearl shell can be directly placed. Such a sample table is desirably the one that fluorescence in the range of wavelength to be measured is not generated, but if there is a part which generates fluorescence, more precise measurement can be conducted by masking (making no fluorescence) all parts but the one to be measured.

Also, the light irradiation part means a part for irradiating the pearl or pearl shell on the arrangement part described above with light from an ultraviolet light (UV) source, and the light from the light source may be directly applied or may be applied through a filter or the like. For example, a filter such as optical filter (cutting the wavelength in the range of 300 nm or longer) may be installed. Also, the conventional light source may be appropriately used as the light source, and the light source and the light irradiation part may be linked, if necessary, by an optical fiber or the like. Alternatively, the light source and the light irradiation part may also be unified.

Conventional spectrofluorophotometers may be used as the fluorescence detector, by which fluorescence in both ultraviolet and visible zones can be measured.

According to the preferred embodiment of the present invention, the fluorescence generated by ultraviolet irradiation is photographed with an (ultraviolet responsive) CCD camera equipped with an optical filter (for example, band-path filter) which transmits the wavelengths in the range of 320 to 360 nm, 420 to 460 nm or 400 to 550 nm in the fluorescence detector. Rapid examination of a large amount of pearl or pearl shells can be realized in this manner.

Furthermore, the images thus photographed, if necessary, may be digitized with an A/D converter and delivered to an analyzer.

According to the preferred embodiment of the present invention, the apparatus according to the present invention further comprises a spectral reflectance detector for measuring the spectral reflectance of a pearl or pearl shell irradiated with ultraviolet light from the light irradiation part described above. In this case, the analyzer is preferably in the form that whether the deterioration of the quality of a pearl or pearl shell to be inspected is due to heat treatment or sunlight irradiation can be clarified by evaluating the measurements of the spectral reflectance spectrum in combination with those of the fluorescence spectrum of the pearl or pearl shell to be inspected.

In the analyzer, the data obtained from the fluorescence detector and/or the spectral reflectance detector are compared with those preliminarily measured for a normal pearl or pearl shell to judge the deterioration degree of the pearl or pearl shell. As the normal data preliminarily measured, the data of the normal pearl or pearl shell having been measured may be kept and used, or normal data may be obtained in every measurement and used.

In the present invention, a commercially available personal computer (PC) or the like may be used as the analyzer and the display.

Also, when the fluorescence of a sample generated by ultraviolet irradiation is detected with a CCD camera equipped with an optical filter (for example, band-path filter) in the detection part, the result may be delivered to the analyzer for image processing with a personal computer (PC) and digitization processing of the brightness of each sample. For digitization processing, either of commercially available or generally available image processing software such as Image 3 and Photoshop may be used. The gradations of the target part of measurement can be averaged with the image processing software (for example, the gradations in an image processing carried out with an 8 bit software are reached up to 256) to use the values thus obtained as the "fluorescence evaluation values" for the judgment.

In this connection, the judgment can be conducted on the basis of the fluorescence evaluation value obtained by measuring a certain area at a measurement position (for example, a circular zone having a diameter of 5 mm).

According to the preferred embodiment of the present invention, the light irradiated from the light irradiation part of the apparatus according to the present invention has a wavelength of 230 to 475 nm.

According to the preferred embodiment of the present invention, the outputs from the analyzer may be displayed by classification corresponding to the deterioration degree of the pearl or pearl shell in the display of the apparatus of the present invention. Thus, the measurement results can be readily comprehended and the test and judgment results can also be comprehended readily.

In this connection, the expression of values attended with "about", "degree" or "around" means herein values which include the variations acceptable by a person skilled in the art for achieving the purpose by setting up the values.

EXAMPLE

The present invention is now described in detail with the following examples without limitation thereto.

Example 1

(1-1) Materials and Methods

20 Akoya pearls having a diameter of 6.0 to 7.0 mm and a nacreous powder sample obtained from the nacre of Akoya oyster shells were used as materials to be inspected. In this connection, about 250 g of the nacreous powder sample was obtained by completely removing the prismatic layer and the pellucid layer portions from pearl shells for 50 individuals of Akoya oyster (3 years oyster) produced by artificial seedling collection and grinding the shells into a size of less than 0.3 mm. The sample was treated basically in darkness at low temperature.

(1-2) Measurement of Reflectance Spectrum

Reflection spectrum was measured in the range of 200 to 550 nm with a spectrophotometer equipped with an integrating sphere unit (V-570, JASCO). In this connection, a mask with a size of 5 mm was used in the measurement.

(1-3) Measurement of Fluorescence Spectrum

Fluorescence spectrum was measured in the range of 300 to 400 nm with a spectrofluorophotometer (FP-750, JASCO). Excitation wavelength was set to 280 nm, and a mask with a size of 5 mm was used in the measurement of fluorescence intensity.

(1-4) Experiment of Heat Treatment

Heat treatment (referred to hereinafter as heat treatment zone) was carried out by leaving a 60 mm×18 mm circular glass petri dish containing 10 pearl samples and 30 g of a nacreous powder sample to stand in a hot air dryer (equipped with a programmed temperature controller E Type, K.K. Isuzu Seisakusho) at 100° C. for 768 hours. The reflectance and fluorescence spectra of the pearl samples were measured before heat treatment and after 6, 12, 24, 48, 96, 192, 384 and 768 hours of the treatment. In this connection, measurement was conducted after the sample was cooled to room temperature.

(1-5) Experiment of Sunlight Irradiation Treatment

Sunlight irradiation treatment (referred to hereinafter as sunlight irradiation zone) was carried out by fixing 10 pearl samples and 30 g of a nacreous powder sample on a xenon tester (SUNTESTER XF-180 CPS, Toyo Seiki Seisaku-Sho, Ltd.) so as the same plane of the samples to be irradiated with artificial sunlight from a xenon light (200V, 1.5 kW, radiation approximated to the spectrum of sunlight by using an anti-reflection coated quartz glass and a special UV filter) at 250 W/m² of irradiance and 35° C. for 768 hours (corresponding to blue scale grade 8, JIS L-0841). The reflectance and fluorescence spectra were measured in the light irradiated plane of the pearl samples before treatment and after 12, 24, 48, 96, 192, 384 and 768 hours of the treatment.

(1-6) Experimental Results (i) Variations of Reflectance Spectra

Typical variations of the reflectance spectra in the heat treatment zone and the sunlight irradiation zone in the pearl samples are shown in FIG. 1.

A maximal absorption was observed at a wavelength of 282 nm in each of the reflectance spectra of the pearl samples before treatment. In the reflectance spectra in the heat treatment zone, the spectral reflectance showed a tendency to ascend throughout the whole wavelength longer than 250 nm from 6 hours after treatment, then the spectral reflectance in the range of 300 to 450 nm with around 322 nm in the center and in the range of 248 to 282 nm with 254 nm in the center were slightly decreased after 12 hours, whereas the spectral reflectance in the visible region of 450 nm or longer showed a tendency to ascend (FIG. 1A).

Figure 1B:
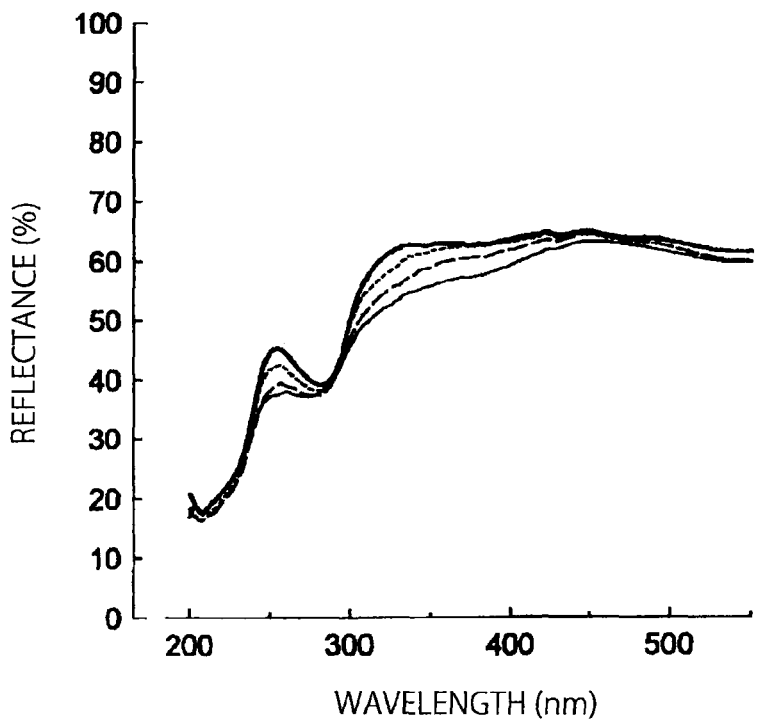

In the sunlight irradiation zone, the spectral reflectances in the range of 322 to 475 nm and in the range of 248 to 282 nm with 254 nm in the center were gradually lowered, and the maximal absorption at around 280 nm which was clearly observed in the pearls before treatment became extremely ambiguous (FIG. 1B).

Figure 2:
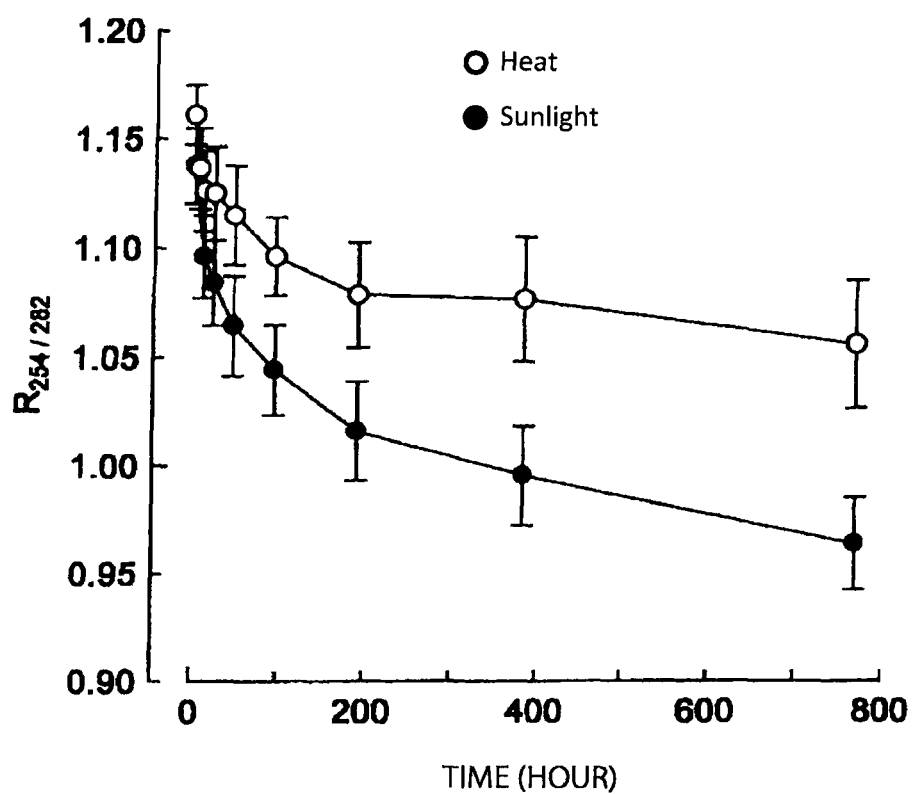
FIG. 2 shows the variations of spectral reflectance around 254 nm along with the time course of treatments with heat and sunlight irradiation in Example 1.

Thus, the ratio ($R_{254/282}$) of the spectral reflectance at a wavelength of 254 nm ($R_{254}$) and 282 nm ($R_{282}$) was obtained, and the variations of the spectral reflectance at around 254 nm with the passage of time of heat and sunlight irradiation treatments are shown in FIG. 2.

In the heat treatment zone, the ratio $R_{254/282}$ was decreased markedly until 12 hours after treatment, but it was slowly decreased afterward. In contrast, in the sunlight irradiation zone, the ratio was markedly decreased until 48 hours after treatment and slowly decreased after that time, but the decreased amount was large as compared with that in the heat treatment zone. Thus, the samples having a ratio lower than 1.0 were increased from 192 hours of treatment, and all samples showed a value lower than 1.0 after 768 hours.

(ii) Variations of Fluorescence Spectra

Typical variations of the fluorescence spectra in the heat treatment zone and the sunlight irradiation zone in the pearl samples are shown in FIG. 3.

Figure 3A:
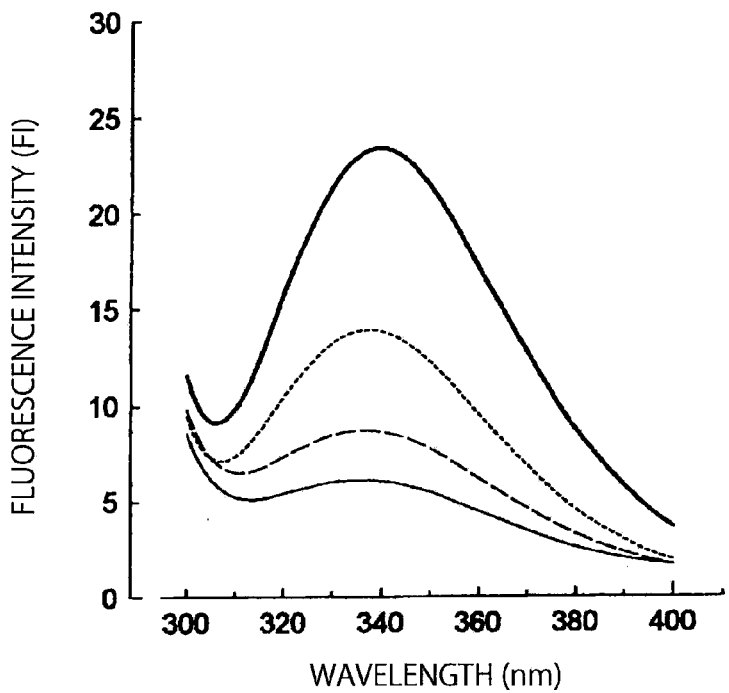
FIG. 3 shows the measurements of fluorescence spectrum in Example 1.
Figure 3B:
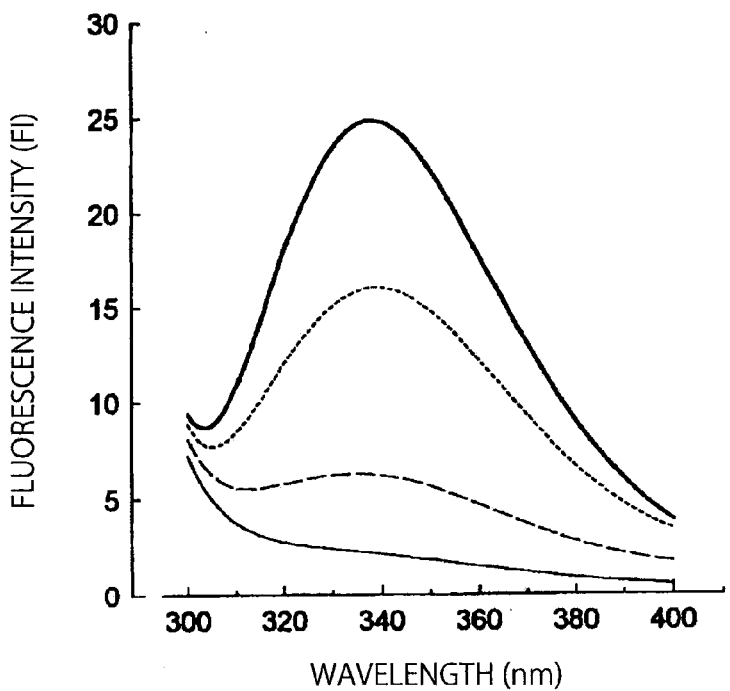

The fluorescence spectrum of the pearl samples before treatment showed a single fluorescence maximum peak at a wavelength of around 340 nm. The fluorescence spectra in both heat treatment and sunlight irradiation zones were weakened along with a blue shift in the fluorescence peak wavelength of up to about 5 nm and showed almost the same characteristic variations (FIGS. 3A and 3B).

Figure 4:
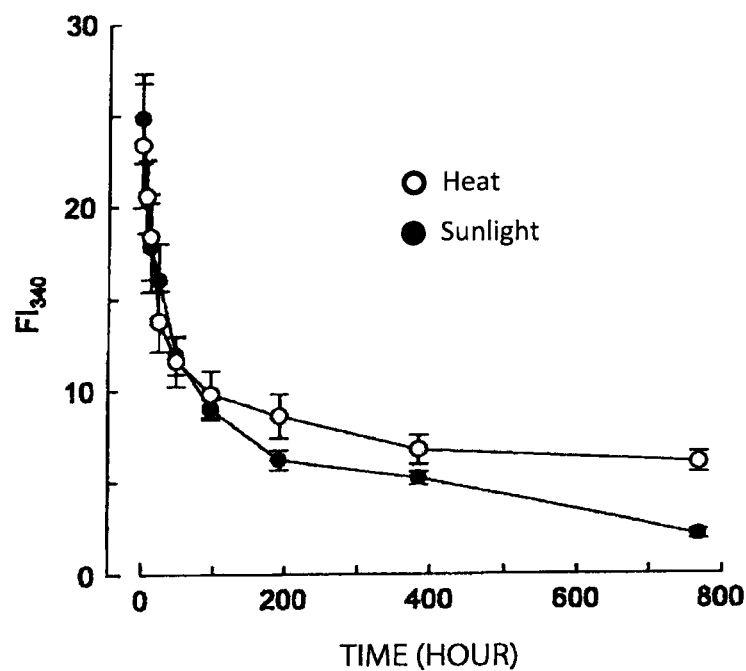
FIG. 4 shows the variations of fluorescence intensity at 340 nm $FI_{340}$ along with the time course of treatments with heat and sunlight irradiation in Example 1.

Therefore, the variations of fluorescence intensity at 340 nm $FI_{340}$ with the passage of time after treatment in both test zones were shown in FIG. 4.

As a result, $FI_{340}$ in both heat treatment and sunlight irradiation zones showed the similar decreasing tendency until 96 hours after treatment, and the decreasing tendency in the heat treatment zone was slightly smaller than that in the sunlight irradiation zone on and after 120 hours. However, little difference was observed in both zones at the end of the inspection.

Example 2

The influence of chemical agents (bleaches) on Akoya pearls was evaluated non-destructively.

In this connection, the methods and apparatuses of measurement were the same as used in Example 1.

Specifically, Akoya pearls (36, untreated pearls having a diameter of 5.5 mm) were prepared and divided into 4 groups. Respective groups were treated under the following conditions: treatment A (bleach concentration: 1.5%, solvent: water), treatment B (bleach concentration: 3.0%, solvent: water), treatment C (bleach concentration: 1.5%, solvent: alcoholic solvent), treatment D (bleach concentration:

3.0%, solvent: alcoholic solvent). In this connection, a commercially available bleach solution usually used in the art was used as the bleaching solution.

As for the pearls under the respective treatment conditions, the ratio $R_{254/282}$ of the spectral reflectance at a wavelength of 254 nm ($R_{254}$) and the spectral reflectance at a wavelength of 282 nm ($R_{282}$) was measured with the passage of time (from the start date of treatment to 40 days after treatment).

Figure 5:
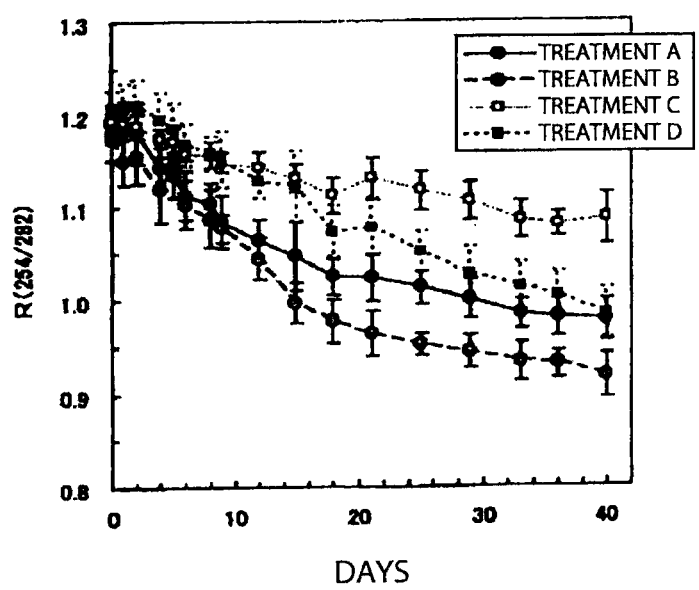
FIG. 5 shows the measurements of the reflectance spectrum in Example 2.

The results are shown in FIG. 5.

It was observed from the results that the ratio $R_{254/282}$ was more markedly lowered in proportion to the treatment term becoming longer from about 3 days after treatment, although the variations of the ratio $R_{254/282}$ of pearls were different depending on the respective treatments.

Furthermore, the variations of fluorescence evaluation value in the ultraviolet range accompanied with the passage of time (from the start date of treatment to 40 days after treatment) were also measured on the pearls under the respective treatment conditions.

The fluorescence evaluation value in the ultraviolet range was measured with an inspection apparatus having the following construction:

Pearl samples were set on a sample table (corresponding to the arrangement part) which was an acrylic plate having a size of 150×150 mm (capable of setting 100 pearls) and equipped with masks (no fluorescent screen) having a diameter of 5 mm, and the pearls to be inspected were irradiated with ultraviolet light in the range of 300 nm or less for about 1 second by using a xenon lamp as a UV light source (corresponding to the light irradiation part) and a filter (cutting light in the range of 300 nm or more). The fluorescence of the pearl to be inspected which was generated by ultraviolet irradiation was detected with an ultraviolet responsive CCD camera (corresponding to the fluorescence detector) equipped with a band-path filter (320 to 360 nm) and the brightness of the respective pearls to be inspected was digitized by the image processing of a personal computer (PC) (corresponding to the analyzer).

In this connection, a commercially available image processing software was used for image processing to carry out the averaging treatment of gradations of parts to be measured (image processing was carried out with an 8 bit software in this case, so that the gradations in an image processing are reached up to 256 and correspond to the values of the processing).

The processed results were digitally displayed on a monitor (corresponding to the display), and the displayed value was treated as the fluorescence evaluation value in the ultraviolet range.

Figure 6:
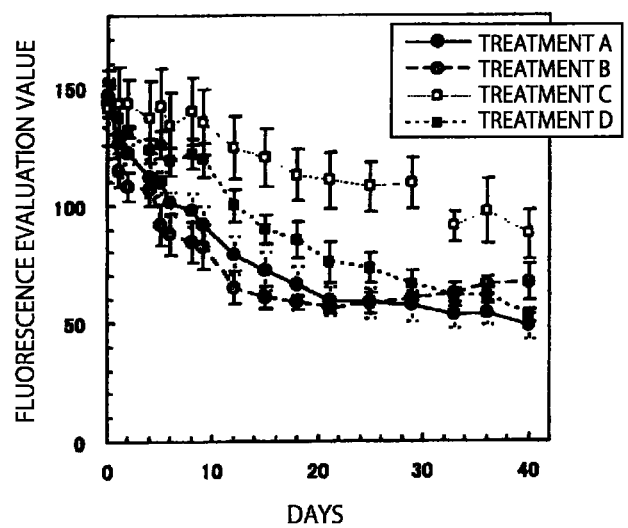
FIG. 6 shows the measurements of the fluorescence spectrum in Example 2.

The results are shown in FIG. 6.

Figure 7:
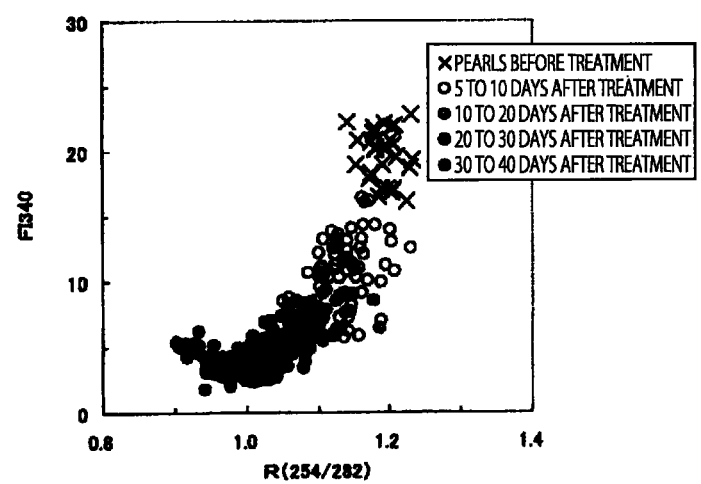
FIG. 7 shows the relationship between the ratio $R_{254/282}$ and $FI_{340}$ obtained in Example 2.

Furthermore, fluorescence intensity at a wavelength of 340 nm ($FI_{340}$) was also measured, and the correlation between the ratio $R_{254/282}$ and $FI_{340}$ is shown in FIG. 7 at the respective cases of before treatment, 5 to 10 days after treatment, 10 to 20 days after treatment, 20 to 30 days after treatment and 30 to 40 days after treatment.

It has been observed from the results that the ratio $R_{254/282}$ and $FI_{340}$ In the pearls treated with the chemical agents (bleaches) were remarkably lowered as the treatment term of pearls were prolonged to 5 days or more.

Example 3

771 normal Silver lipped pearls and 8 deteriorated Silver lipped pearls were prepared (respectively obtained from commercial sources), and the ratios of the spectral reflectances $R_{254/282}$ and the fluorescence evaluation value in the ultraviolet range were measured in the same manner as in Example 2.

Figure 8:
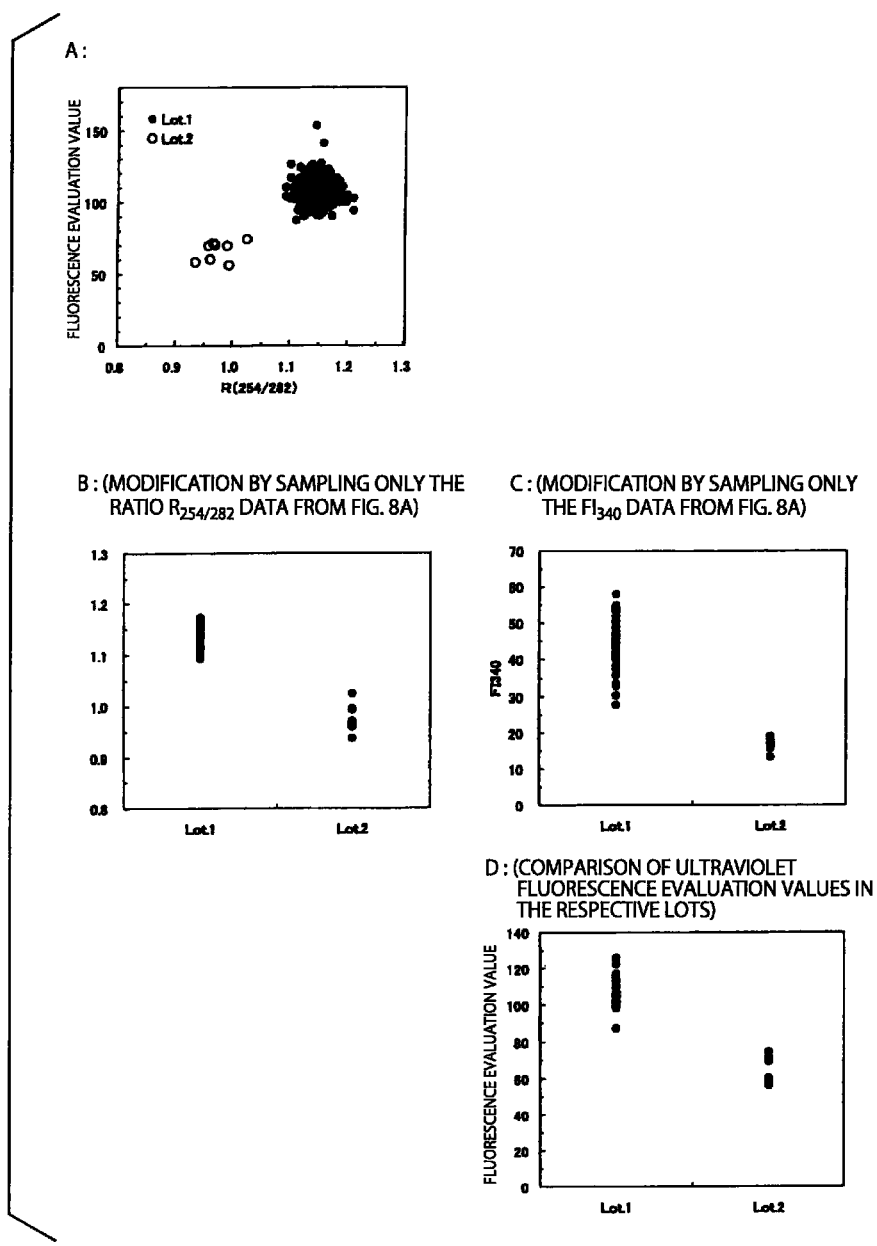
FIG. 8 shows the results of Example 3.

The results are shown in FIG. 8A.

Furthermore, the ratio of the spectral reflectances $R_{254/282}$, the fluorescence intensities at a wavelength of 340 nm ($FI_{340}$) and the fluorescence evaluation values in the ultraviolet range of 74 pearls sampled from the normal Silver lipped pearls by random sampling and the 8 deteriorated Silver lipped pearls were measured in the same manner as in Example 2.

The results are shown in FIGS. 8B to 8D.

It may be judged from the results that the pearls have been deteriorated, as the pearls of Lot 2 (○) have the ratio $R_{254/282}$, $FI_{340}$ and the fluorescence evaluation value in the ultraviolet range lower than those of the other lot.

Example 4

3 lots of Fresh water pearls were prepared (30 pearls, obtained from commercial sources), and the ratios of the spectral reflectances $R_{254/282}$ and the fluorescence intensities at a wavelength of 340 nm ($FI_{340}$) were measured in the same manner as in Example 2.

Figure 9:
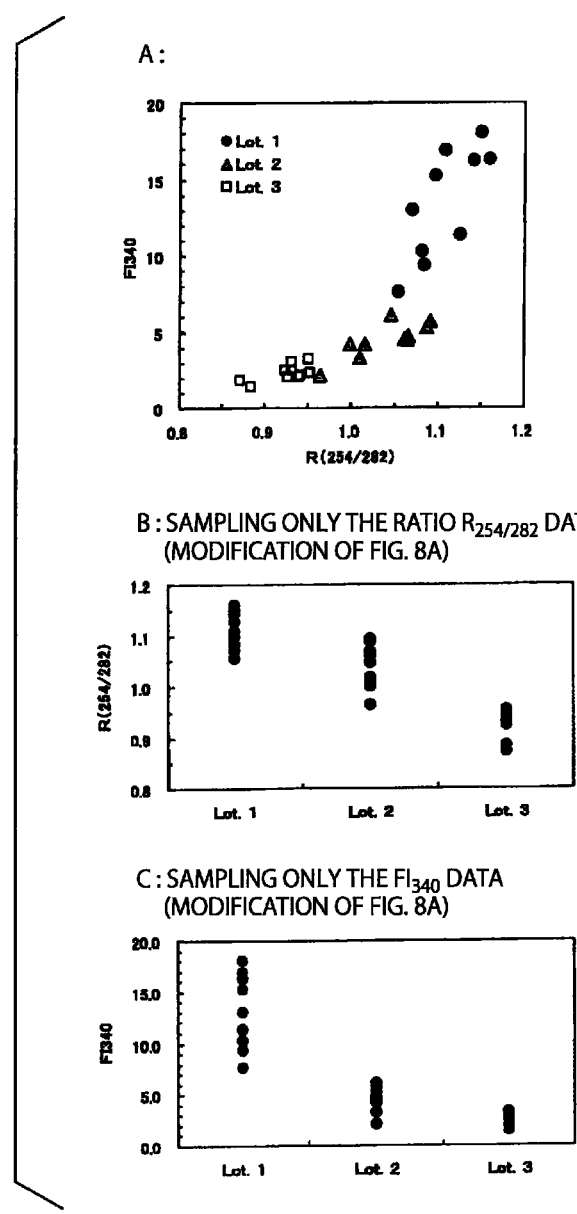
FIG. 9 shows the results of Example 4.

The results are shown in FIG. 9 (FIGS. 9A to 9C).

It may be judged from the results that Lots 2 and 3 have been still more deteriorated as compared to Lot 1 as these values have a decreasing tendency in an order of Lot 1>Lot 2>Lot 3.

Example 5

Akoya pearls before treatment and pearls treated with fluorescent brighteners were prepared (73 pearls, obtained from commercial sources), and fluorescence in the visible range was measured to compare the fluorescence evaluation values in the visible range.

In this connection, the fluorescence evaluation values in the visible range were measured with an inspection apparatus having the following construction:

Pearl samples were set on a sample table (corresponding to the arrangement part) of a camera *obscura* and irradiated with UV light at a wavelength of 365 nm by using an LED (corresponding to the light irradiation part). The fluorescence of the pearl to be inspected which was generated by ultraviolet irradiation was detected with a CCD camera (corresponding to the fluorescence detector) equipped with a band-path filter (420 to 460 nm) and the brightness of the respective pearls to be inspected was digitized by the image processing of a personal computer (PC) (corresponding to the analyzer).

In this connection, a commercially available image processing software was used for image processing to carry out the averaging treatment of gradations of parts to be measured (image processing was carried out with an 8 bit software in this case, so that the gradations in an image processing are reached up to 256 and correspond to the values of the processing).

The processed results were digitally displayed on a monitor of a PC (corresponding to the display), and the displayed value was treated as the fluorescence evaluation value in the visible range.

Figure 10:
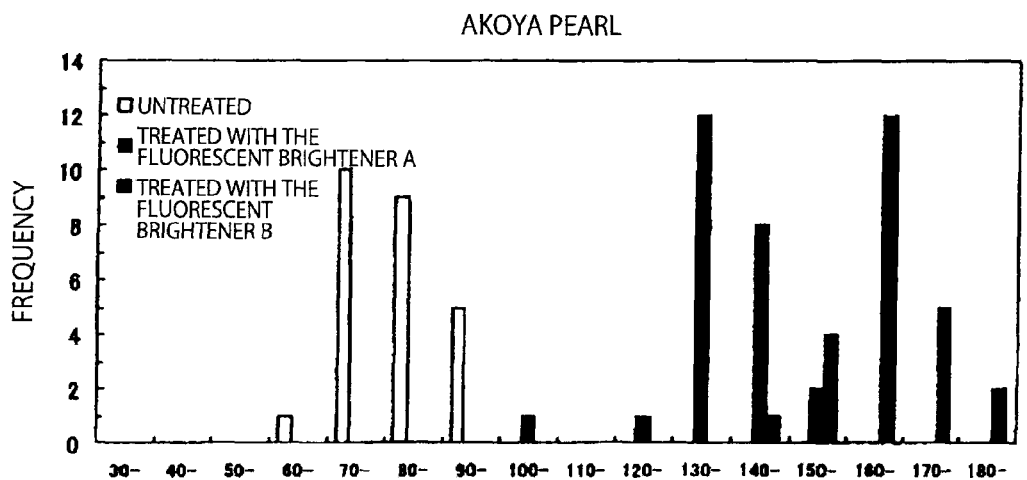
FIG. 10 shows the results of Example 5.
Figure 11:
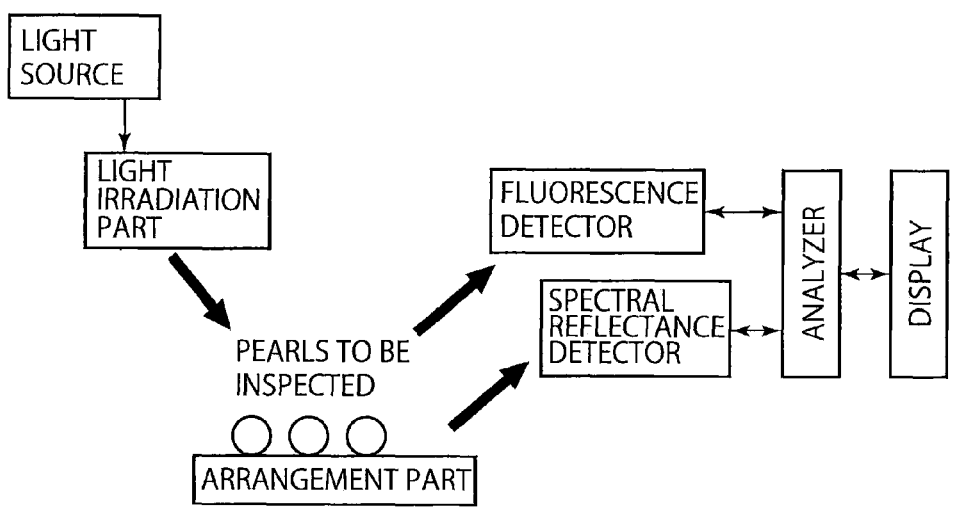
FIG. 11 shows the conceptional diagram of the apparatus of the present invention.

The results are shown in FIG. 10.

It has been observed from the results that the Akoya pearls (untreated pearls) had the visible fluorescence evaluation value digitized with a fluorescence evaluation apparatus in the range of 100 or less, whereas the pearls (2 types) treated with a fluorescent brightener had markedly high fluorescence evaluation value.

What is claimed is:

1. A method for non-destructive judgment of pearl quality, comprising the steps of measuring at least one spectrum selected from the group consisting of an ultraviolet-visible reflection spectrum being a spectral reflectance in the range of 250 to 260 nm (Ra), a spectral reflectance in the range of 270 to 290 nm (Rb), and a ultraviolet-visible fluorescence spectrum of a pearl or pearl shell to be inspected, and comparing at least one value selected from the group consisting of spectral reflectance ratio (Ra/Rb), spectral reflectance difference (Ra−Rb), and fluorescence intensity with those preliminarily measured for a normal pearl or pearl shell,
- wherein the Ra and the Rb of a pearl or pearl shell to be inspected are measured to calculate the spectral reflectance ratio (Ra/Rb) or the spectral reflectance difference (Ra−Rb),
- wherein the fluorescence intensity of the fluorescence spectrum in the range of 320 to 360 nm is measured using an excitation wavelength in the range of 250 to 300 nm, and
- wherein the degree of the deterioration of the pearl or pearl shell to be inspected is judged based on at least one value selected from the group consisting of the spectral reflectance ratio (Ra/Rb), spectral reflectance difference (Ra−Rb), and fluorescence intensity.

2. A method according to claim 1, wherein the reflection spectrum and fluorescence spectrum of nacreous proteins of the pearl or pearl shell to be inspected are measured.

3. A method according to claim 2, which comprises judging whether the deterioration of the pearl or pearl shell to be inspected is due to heat treatment or sunlight irradiation, by evaluating the combination of the measurement obtained from the ultraviolet-visible reflection spectrum of the pearl or pearl shell to be inspected and the measurement obtained from the ultraviolet-visible fluorescence spectrum of the pearl or pearl shell to be inspected.

4. A method according to claim 2, wherein fluorescence generated by ultraviolet light is photographed by a CCD camera equipped with an optical filter through which light in the range of 320 to 360 nm is transmitted, and the result is digitized for judgment based on this result.

5. A method according to claim 1, which comprises judging whether the deterioration of the pearl or pearl shell to be inspected is due to heat treatment or sunlight irradiation, by evaluating the combination of the measurement obtained from the ultraviolet-visible reflection spectrum of the pearl or pearl shell to be inspected and the measurement obtained from the ultraviolet-visible fluorescence spectrum of the pearl or pearl shell to be inspected.

6. A method according to claim 1, wherein fluorescence generated by ultraviolet light is photographed by a CCD camera equipped with an optical filter through which light in the range of 320 to 360 nm is transmitted, and the result is digitized for judgment based on this result.

7. The method of claim 1, wherein the deterioration of the pearl or pearl shell to be inspected is due to at least one selected from the group consisting of heat treatment, sunlight irradiation, bleaching treatment, coloring treatment, treatment with a fluorescent brightener and treatment with a chemical agent.

* * * * *